United States Patent [19]

Hall et al.

[11] 4,428,966

[45] Jan. 31, 1984

[54] USE OF SUBSTITUTED CYCLOHEXYL CARBOALKOXY KETONE IN AUGMENTING OR ENHANCING THE AROMA OR TASTE OF FOODSTUFFS

[75] Inventors: John B. Hall, Rumson; Mark A. Sprecker, Sea Bright, both of N.J.

[73] Assignee: International Flavors & Fragrances Inc., New York, N.Y.

[21] Appl. No.: 474,161

[22] Filed: Mar. 10, 1983

Related U.S. Application Data

[62] Division of Ser. No. 375,767, May 6, 1982.

[51] Int. Cl.³ .............................................. A23L 1/235
[52] U.S. Cl. ......................................... 426/3; 426/538
[58] Field of Search ...................................... 426/3, 538

[56] References Cited

U.S. PATENT DOCUMENTS 4,064,281 12/1977 Hall et al. ........................... 426/538

Primary Examiner—Joseph M. Golian
Attorney, Agent, or Firm—Arthur L. Liberman

[57] ABSTRACT

Described is a process for augmenting or enhancing the aroma or taste of raspberry flavored foodstuffs or chewing gums by adding to a foodstuff or chewing gum an aroma or taste augmenting or enhancing quantity of at least one compound having the structure:

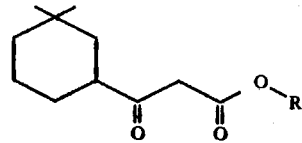

wherein R represents $C_1$-$C_3$ alkyl.

2 Claims, 5 Drawing Figures

FIG.1

GLC PROFILE FOR EXAMPLE I BULKED FRACTIONS 5 AND 6.

FIG. 4

IR SPECTRUM FOR EXAMPLE II.

FIG. 5
NMR SPECTRUM FOR EXAMPLE III.

USE OF SUBSTITUTED CYCLOHEXYL CARBOALKOXY KETONE IN AUGMENTING OR ENHANCING THE AROMA OR TASTE OF FOODSTUFFS

This is a divisional of application Ser. No. 375,767, filed May 6, 1982.

BACKGROUND OF THE INVENTION

U.S. Pat. Nos. 4,064,281 issued Dec. 20, 1977 and 4,102,928 issued July 25, 1978 describe processes for preparing compounds defined according to the structure:

in low yields by reaction of an allylic halide with acetyl-3,3-dimethycyclohexane in the presence of a phase transfer catalyst. Primarily U.S. Pat. No. 4,064,281 teaches the reaction:

The compound having the structure:

is prepared incidentally to that reaction. Dutch Published Application No. 7500838 discloses the preparation of the compound having the structure:

in a manner different in kind from the instant process giving rise to yields far below the yields produced according to the instant process.

In addition, there is a continuing search for compositions which can vary, fortify, modify, enhance, augment or otherwise improve the flavor and aroma of foodstuffs, medicinal products, chewing gums, toothpastes and chewing tobaccos. To be satisfactory, such compositions should be stable, non-toxic and blendable with other ingredients to provide its own unique flavor and aroma nuance without detracting from the co-ingredients. Preferably, such compositions should be naturally occurring or be present in natural foodstuffs so that its ingestible safety can be readily recognized. These materials should be capable of being synthesized in a simple and economical manner. The need for safe flavors in the raspberry, vanilla, black olive and honey area is well known particularly in the ice cream, liqueur and yogurt flavor areas and in the cold beverage area; as well as in the salad dressing area. More specifically, there is a need for the development of non-toxic materials which can replace natural materials not readily available having sweet, woody, green, vanilla, celery-like, honey and fruity aroma characteristics and sweet, woody/cedarwood-like, tobacco-like, fruity, lavender, black olive, vanilla-like and honey flavor characteristics.

Dutch Application No. 7500838 discloses the preparation of the compound having the structure:

and discloses its use in perfumery and in augmenting foodstuff flavors. The perfumery use of this compound and other members of its class is described as "floral, green, herbaceous and chypre". The use as a galbanum component is also disclosed therein.

However, nothing in the prior art discloses the flavor use of the intermediates having the structure:

BRIEF DESCRIPTION OF THE DRAWINGS

FIG. 2 is the NMR spectrum for the compound having the structure:

produced according to Example I.

FIG. 3 is the NMR spectrum for the compound having the structure:

produced according to Example II.

FIG. 4 is the infra-red spectrum for the compound having the structure:

produced according to Example II.

THE INVENTION

Our invention relates to a process for preparing a compound having the structure:

comprising the steps of reacting the compound having the structure:

with a di-lower alkyl carbonate having the structure:

in order to produce a ketoester having the structure:

using the ketoester for its organoleptic properties or further reacting the ketoester with an allyl halide having the structure:

to produce a substituted ketoester having the structure:

saponifying the substituted ketoester with a base thereby forming a keto carboxylic acid salt having the structure:

wherein M' represents alkali metal; wherein R represents $C_1$–$C_3$ lower alkyl; and wherein X represents chloro, bromo or iodo hydrolyzing the keto carboxylic acid salt with acid to form the substituted keto carboxylic acid having the structure:

heating and decarboxylating the resulting carboxylic acid to form the compound having the structure:

The compound defined according to the generic structure:

wherein R represents $C_1$–$C_3$ alkyl are particularly useful in augmenting or enhancing the aroma or taste of raspberry, vanilla, black olive and honey flavors particularly insofar as they provide sweet, woody/cedarwood, fruity, green, cooked celery, vanilla, and honey aroma nuances and sweet, woody/cedarwood, tobacco-like, fruity, lavendar, black olive, vanilla and honey flavor nuances at 2 ppm and piney, apple, lavender, woody and pineapple nuances at 10 ppm.

The compound having the structure:

provides strong, green, galbanum-like, fruity, and pineapple aroma with herbal and fir balsam undertones in perfumery and for perfumed articles.

The process for our invention can be illustrated by the reaction sequences:

wherein R represents $C_1$–$C_3$ lower alkyl; M represents alkali metal or alkaline earth metal; x represents 1 or 2; X represents chloro bromo or iodo; and M' represents alkali metal and R represents $C_1$–$C_3$ lower alkyl.

In carrying out the reaction of the di-alkyl carbonate having the structure:

with the 1-acetyl-3,3-dimethylcyclohexane having the structure:

the di-alkyl carbonate can be used as the solvent so that excess di-alkyl carbonate is preferably used. The reaction is carried out using as an additional reagent, an alkali metal hydride such as sodium hydride, potassium hydride or an alkaline earth metal hydride catalyst such as calcium hydride or magnesium hydride. The reaction temperature may vary from 25° C. up to 100° C. but the reaction is preferably carried out at reflux conditions. The mole ratio of 1-acetyl-3,3-cyclohexane:alkali metal hydride or alkaline earth metal hydride:di-alkyl carbonate may vary from about 1:2:1 up to about 1:2:2.

In carrying out the reaction of the thus formed keto-ester defined according to the structure:

the reaction with the allyl halide having the structure:

is carried out in the presence of an alkali metal alkoxide such as sodium methoxide, sodium ethoxide, potassium methoxide, potassium ethoxide, or potassium t-butoxide or an alkali metal hydride such as sodium hydride, potassium hydride or lithium hydride or an alkali earth metal hydride such as calcium hydride or magnesium hydride in order to form the substituted ketoester defined according to the structure:

The mole ratio of ketoester having the structure:

allyl halide:alkali metal alkoxide or alkali metal hydride or alkaline earth metal hydride is preferably 1:1:1. This particular reaction preferably takes place in the presence of an inert solvent which will not react with the other reactants such as toluene, benzene or xylene.

In carrying out this reaction, a small amount of compound having the structure:

is formed. This material may be removed by distillation from the reaction mass at this point or may be carried along in the subsequent reactions.

The saponification of the substituted ketoester to form the substituted keto carboxylic acid sodium salt defined according to the structure:

is carried out in the presence of a base such as sodium hydroxide or potassium hydroxide in aqueous media according to standards saponification conditions. The resulting saponified material is then hydrolyzed in the presence of acid under standard hydrolysis conditions known in the art using such mineral acid as sulfuric acid or hydrochloric acid in order to form the substituted keto carboxylic acid defined according to the structure:

This material is then decarboxylated according to standard decarboxylation conditions in order to form the compound having the structure:

As a by-product, the compound having the structure:

is formed during the reaction as well and this material may be either used together with the compound having the structure:

for their organoleptic properties in admixture, or the material having the structure:

can be distilled out of the reaction mass at this point leaving pure compound having the structure:

Referring to the novel compounds of our invention defined according to the structure:

having novel organoleptic uses, the compound having the structure:

will hereinafter be referred to as keto carboxylic acid esters.

When the keto carboxylic acid esters of our invention are used as food flavor adjuvants, the nature of the co-ingredients included with the keto carboxylic acid esters of our invention in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the keto carboxylic acid esters of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stablizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrans, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes and ketals and acetals thereof, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, cis-ethylidene-cis-3-hexenal, cis-ethylidene-trans-3-hexenal, cis-ethylidene-trans-3-heptenal, cis-ethylidene-trans-3-heptenal-diethyl-acetal, cis-3-ethylidene-4-octenal, beta-cyclohomocitral, 2-pentanone, 2-pentenal an propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl actate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, lphellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and other acetals (e.g., 1,1-diethoxy-ethane, 1,1-dimethoxy-ethane and dimethoxy-methane).

The specific flavoring adjuvant selected for use may be either solid or liquid depending upon the desired physical form of the ultimate product, i.e., foodstuff, whether simulated or natural, and should, in any event, (i) be organoleptically compatible with the keto carboxylic acid esters of our invention by not covering or spoiling the organoleptic properties (aroma and/or taste) thereof; (ii) be non-reactive with the keto carboxylic acid esters of our invention, and (iii) be capable of providing an environment in which the keto carboxylic acid esters of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of keto carboxylic acid esters of our invention employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purpose of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the keto carboxylic acid esters of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of keto carboxylic acid esters of our invention ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the keto carboxylic acid esters of our invention are added to the foodstuff as an integral component of a flavoring composition, it is, of course, essential that the total quantity of flavoring composition employed be sufficient to yield an effective keto carboxylic acid ester concentration in the foodstuff product.

Food flavoring compositions prepared in accordance with the present invention preferably contain the keto carboxylic acid esters of our invention in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the keto carboxylic acid esters of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like and the keto carboxylic acid esters of our invention in a dry blender until the requisite degree of uniformity is achieved.

It is presently preferred to combine with the keto carboxylic acid esters of our invention, the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
isoamyl acetate;
Cis-ethylidene-cis-3-hexenal;
Cis-ethylidene-trans-3-hexenal;
Cis-ethylidene-trans-3-heptenal;
Cis-ethylidene-trans-3-heptenal-dietylacetal;
Cis-3-ethylidene-4-octenal;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
Damascone (1-crotonyl-2,2,6-trimethylcyclohex-1-one)
Damascenone (1-crotonyl-2,2,6-trimethylcyclohexa-1,5-diene)
Beta-cyclohomocitral (2,2,6-trimethylcylohex-1-ene carboxaldehyde )
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-Hydroxy-4-methylpentyl) norbornadiene prepared according to U.S. Pat. No. 3,886,289 issued May 27, 1975.

The following Examples I–III serve to illustrate methods for carrying out the processes of our invention. The following Example IV, et seq serve to illustrate organoleptic uses of the novel compounds of our invention. The invention is to be considered restricted to these examples only as indicated in the appended claims. All parts and percentages given herein are by weight unless otherwise specified.

EXAMPLE I

Preparation of 1(4-Pentenoyl)-3,3-Dimethylcyclohexane and

-continued (wherein R represents methyl; wherein X represents chloro; wherein M represents sodium; wherein R' represents methyl; wherein x represents the integer 1; wherein M' represents sodium).

Into a 10 liter reaction vessel equipped with stirrer, thermometer, and reflux condenser is placed 504 grams of 50% sodium hydride and 5 liters of toluene. The resulting mixture is heated to 50° C. and 540 grams (6 moles) of dimethylcarbonate is slowly added. The reaction mass is then heated to 80° C. and while maintaining the reaction mass at 80° C., 770 grams (5 moles) of 1-acetyl-3,3-dimethylcyclohexane is added to the reaction mass. 12 Ml of methanol is then added to the reaction mass and the reaction mass is then stirred for a period of 13 hours, at 80° C.

Over a period of 0.5 hours while maintaining the reaction mass at 70° C., 420.7 grams (5.5 moles) of allyl chloride is added to the reaction mass. The reaction mass is then stirred at 70° C. for a period of 8 hours.

The reaction mass is then admixed with 760 grams (12 moles) of sodium hydroxide and 1000 grams of water and refluxed with water for a period of 3 hours. The reaction mass is then slowly quenched with concentrated hydrochloric acid until the pH is 1. The reaction product is then heated until no carbon dioxide is evolved. The reaction mass is washed as follows:
2 liters water
2 liters 10% sodium carbonate
The reaction product is then distilled on an 18" Goodloe column yielding the following fractions:

| Fraction No. | Vapor Temp. (0° C.) | Liquid Temp. (0° C.) | Vacuum mm.Hg. Pressure | Reflux Ratio | Wgt. of Fractions |
|---|---|---|---|---|---|
| 1 | 50/46 | 80/85 | 1.8 | 9:1 | 60.9 |
| 2 | 50/46 | 80/85 | 1.8 | 4:1 | 37.9 |
| 3 | 72 | 105 | 1.8 | 4:1 | 68.3 |
| 4 | 72 | 112 | 1.8 | 9:1 | 13.6 |
| 5 | 71 | 109 | 1.7 | 9:1 | 13.5 |
| 6 | 70 | 98 | 1.7 | 9:1 | 22.5 |

-continued

| Fraction No. | Vapor Temp. (0° C.) | Liquid Temp. (0° C.) | Vacuum mm.Hg. Pressure | Reflux Ratio | Wgt. of Fractions |
|---|---|---|---|---|---|
| 7 | 73 | 99 | 1.7 | 9:1 | 26.7 |
| 8 | 75 | 100 | 1.7 | 9:1 | 23.4 |
| 9 | 78 | 101 | 1.7 | 9:1 | 21.7 |
| 10 | 81 | 104 | 1.7 | 9:1 | 25.8 |
| 11 | 81 | 105 | 1.7 | 9:1 | 19.8 |
| 12 | 81 | 105 | 1.7 | 1:1 | 17.2 |
| 13 | 81 | 107 | 1.7 | 1:1 | 17.0 |
| 14 | 81 | 110 | 1.7 | 1:1 | 26.3 |
| 15 | 80 | 115 | 1.7 | 1:1 | 20.0 |
| 16 | 80 | 130 | 1.7 | 1:1 | 26.0 |
| 17 | 80 | 175 | 1.7 | 1:1 | 15.0 |
| 18 | 75 | 220 | 1.7 | 100% | 15.4 |

Figure 1:
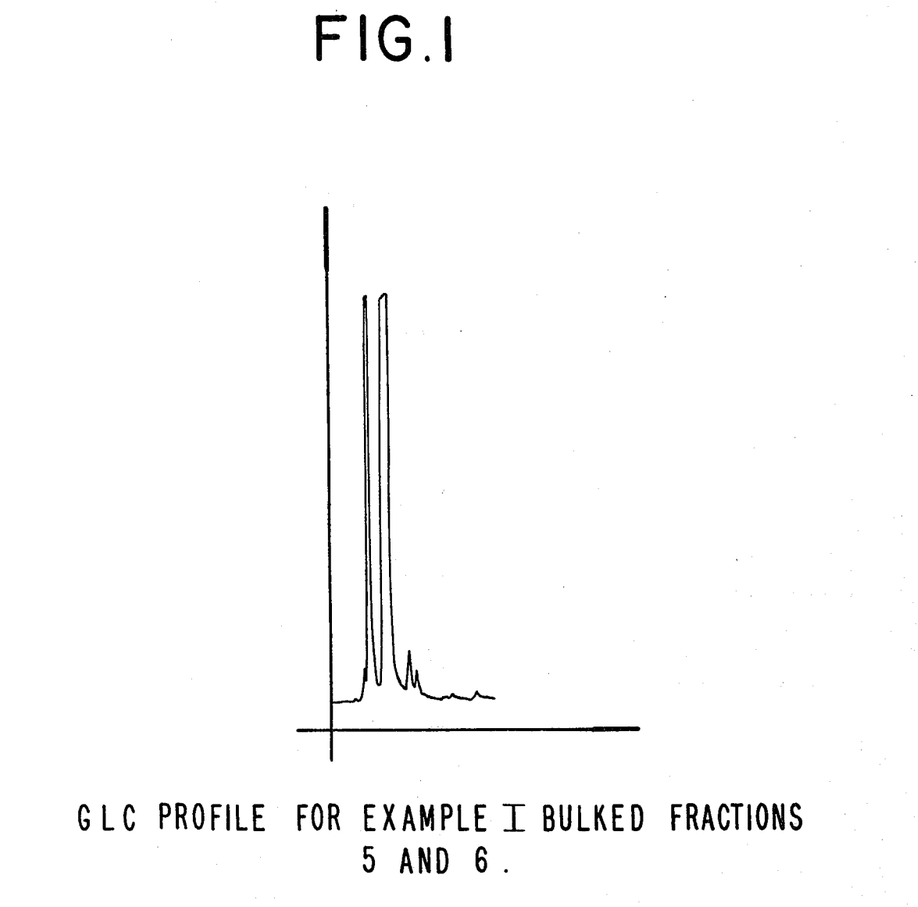
FIG. 1 is the GLC profile for bulked fractions 5 and 6 of the distillation product of the reaction product (Rushover Distillation) for Example I containing the compounds having the structures.
Figure 2:
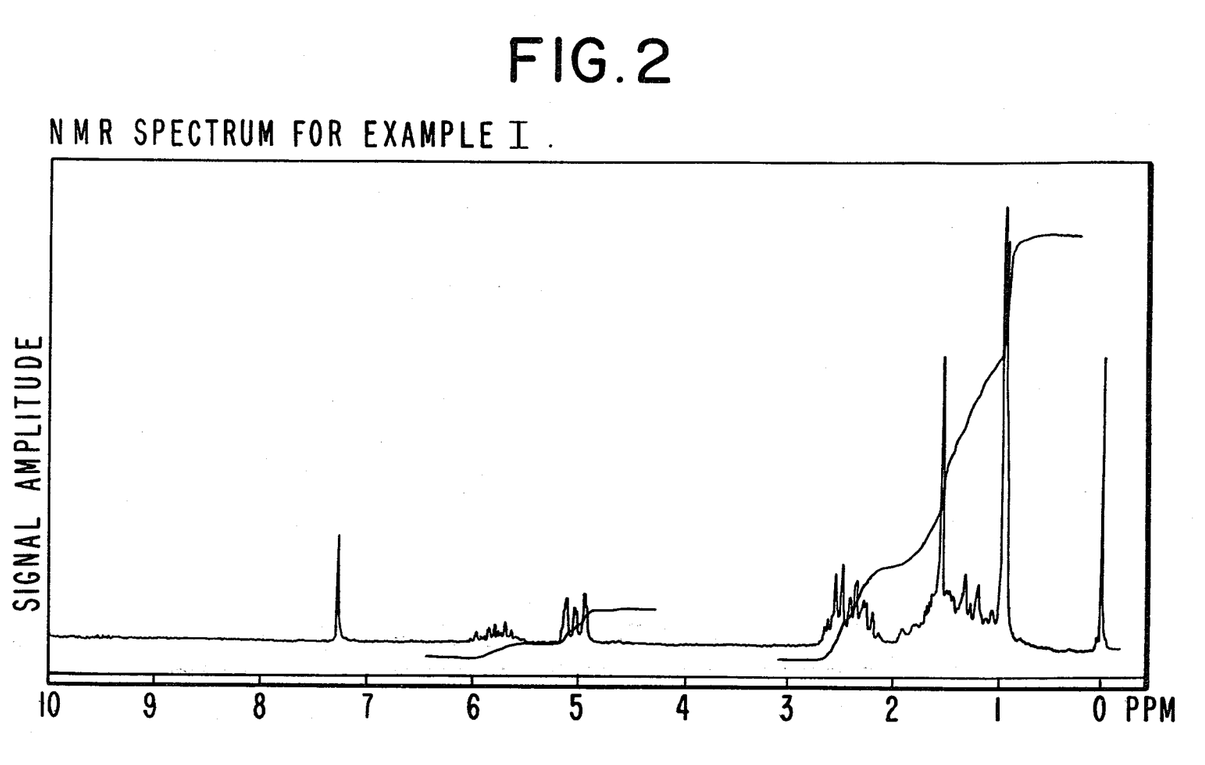

Fractions 1–8 (weighing 262.3 grams) are the product having the structure:

Fractions 9–18 (weighing 204.2 grams) are the product having the structure:

FIG. 1 is the GLC profile for the reaction product prior to distillation but subsequent to a "rushover" distillation carried out prior to the foregoing distillation. This GLC profile represents bulked fractions 5 and 6, a mixture of the compounds having the structures:

FIG. 2 is the NMR spectrum for the compound having the structure:

EXAMPLE II

Preparation of 1-(Carboethoxy Acetyl)-3,3-Dimethylcyclohexane

Reaction:

Into a 2 liter reaction flask equipped with a stirrer, thermometer, reflux condenser and heating mantle is placed 88 grams (2.2 moles) of 55% sodium hydride and 1.0 liters of benzene. The resulting reaction mass is heated to reflux and while refluxing, 236 grams (1.2 moles) of diethylcarbonate is added.

Over a 85 minute period at reflux, 154 grams (1 mole) of 1-acetyl-3,3-dimethylcyclohexane is added to the reaction mass. The reaction mass is refluxed for an additional 4.25 hours.

At the end of the reaction, the reaction mass is washed with 1 liter of water and the organic layer is separated from the aqueous layer. The reaction mass is first distilled on a 2" splash column yielding the following fractions:

| Fraction No. | Vapor Temp. (°C.) | Liquid Temp. (°C.) | Vacuum mm.Hg. Pressure | Wgt. of Fractions |
|---|---|---|---|---|
| 1 | 25/80 | 30/45 | 105 | — |
| 2 | 105 | 130 | 1.9 | 29.7 |
| 3 | 112 | 140 | 1.9 | 31.2 |
| 4 | 135 | 185 | 1.9 | 57.3 |
| 5 | 200 | 227 | 1.9 | 69.5 |
| 6 | 220 | 226 | 1.9 | 4.5 |

The resulting product is then fractionally distilled yielding the following fractions:

| Fraction No. | Vapor Temp. (°C.) | Liquid Temp. (°C.) | Vacuum mm.Hg. Pressure | Reflux Ratio |
|---|---|---|---|---|
| 1 | 108 | 148 | 2.2 | 9:1 |
| 2 | 110 | 170 | 1.5 | 9:1 |
| 3 | 112 | 186 | 1.5 | 9:1 |
| 4 | 116 | 214 | 1.5 | 4:1 |
| 5 | 154 | 220 | 1.5 | 4:1 |
| 6 | 162 | 223 | 1.5 | 4:1 |
| 7 | 193 | 224 | 1.5 | 4:1 |
| 8 | 202 | 241 | 1.5 | 4:1 |
| 9 | 210 | 250 | 1.5 | 4:1 |
| 10 | 213 | 250 | 1.5 | 4:1 |

Figure 3:
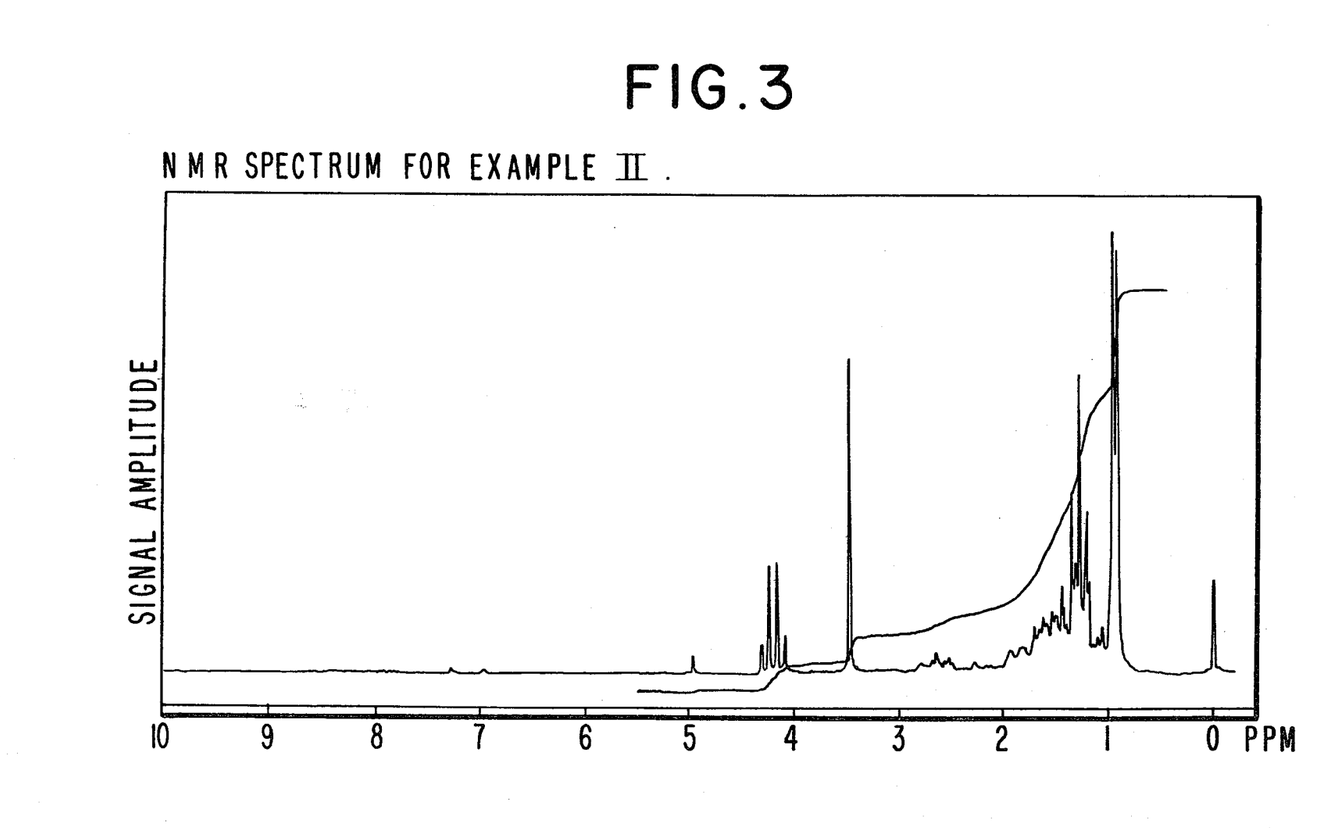

FIG. 3 is the NMR spectrum for the reaction product having the structure:

(solvent: CDCl$_3$; field strength 100 MHz).

Figure 4:
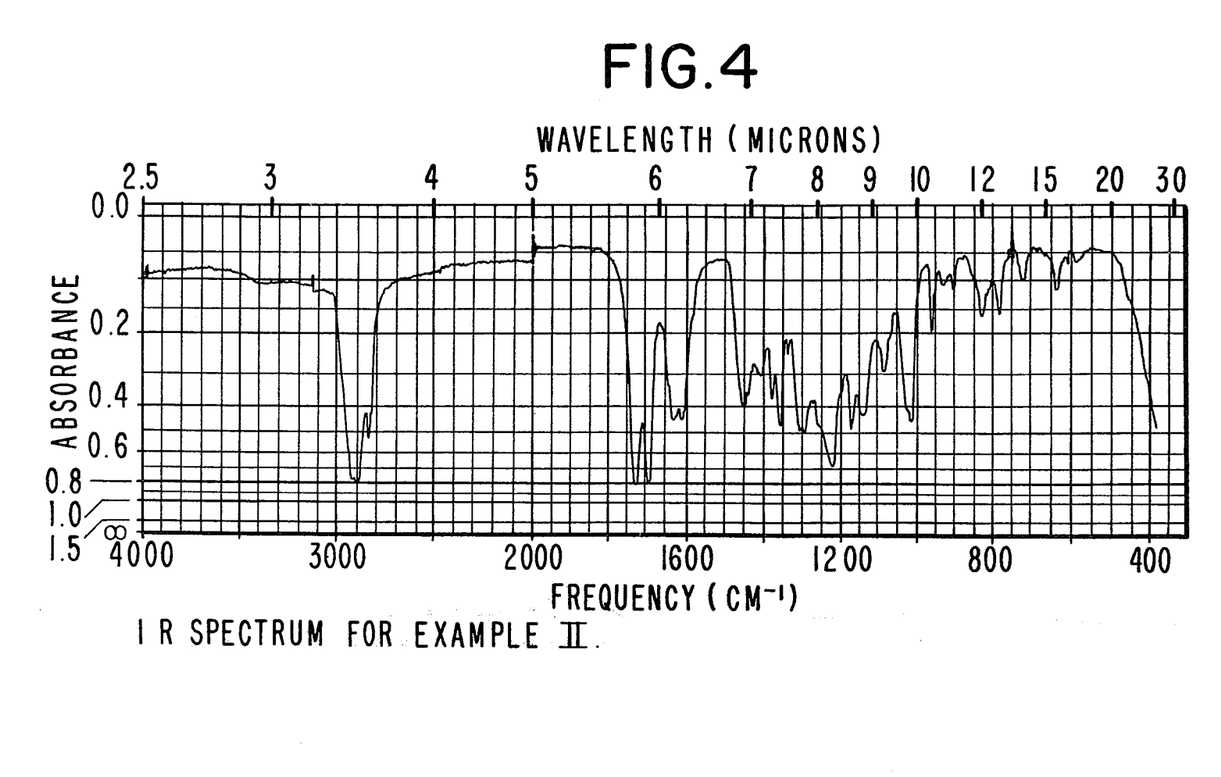

FIG. 4 is the infra-red spectrum for the compound having the structure:

EXAMPLE III

Preparation of 1-Carbomethoxyacetyl-3,3-Dimethylcyclohexane

Reaction:

Into a 5 liter reaction vessel equipped with stirrer, thermometer and reflux condenser is placed 250 grams (5.5 moles) of sodium hydride and 1.6 liters of benzene. The reaction mass is heated to reflux (76° C.) and while refluxing, 500 grams (5.5 moles) of dimethylcarbonate is added to the reaction mass slowly; followed by 770 grams of 1-acetyl-3,3-dimethylcyclohexane (5.0 moles). The reaction mass is refluxed for a period of 4 hours. At the end of the 4 hour reflux period 360 grams (6 moles) of acetic acid is added to the reaction mass. The reaction mass is then admixed with 1000 ml water and the organic phase is separated from the aqueous phase. The reaction mass is then distilled yielding the following fractions:

| Fraction No. | Vapor Temp. (0° C.) | Liquid Temp. (0° C.) | Vacuum mm. Hg. Pressure |
|---|---|---|---|
| 1 | 80 | 97 | 760 |
| 2 | 105 | 150 | 2 |
| 3 | 110 | 150 | 2 |
| 4 | 140 | 150 | 2 |
| 5 | 140 | 150 | 2 |
| 6 | 157 | 170 | 2 |
| 7 | 160 | 178 | 2 |
| 8 | 178 | 179 | 2 |
| 9 | 178 | 179 | 2 |
| 10 | 178 | 179 | 2 |

| Fraction No. | Vapor Temp. (0° C.) | Liquid Temp. (0° C.) | Vacuum mm. Hg. Pressure |
|---|---|---|---|
| 11 | 170 | 240 | 2 |

Fractions 2 and 3 are disgarded and Fractions 4–10 are bulked for organoleptic use.

Figure 5:
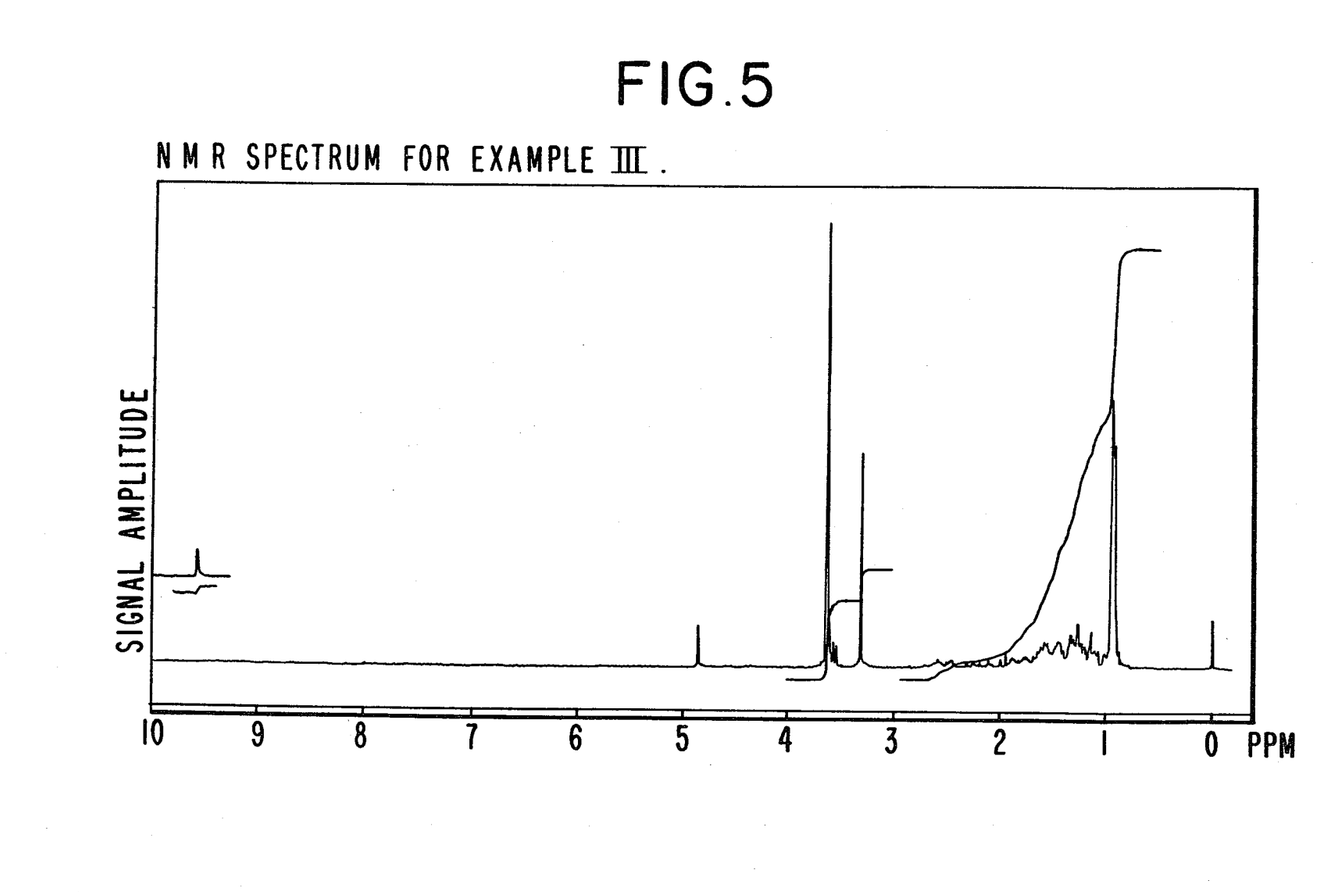
FIG. 5 is the NMR spectrum for fraction 10 of the distillation product of the reaction product of Example III, for the compound having the structure.

FIG. 5 is the NMR spectrum for Fraction 10 of the foregoing distillation (solvent: CFCl₃; field strength 100 MHz). The structure of the compound produced herein is:

EXAMPLE IV

Raspberry Flavor Formulation

The following basic raspberry flavor formulation is produced:

| Ingredient | Parts by Wgt. |
|---|---|
| Vanillin | 2.0 |
| Maltol | 5.0 |
| Parahydroxybenzylactone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

The compound having the structure:

prepared according to Example II is added to half of the above formulation at the rate of 2.0%. The formulation with the carboethoxyacetyl-3,3-dimethylcyclohexane is compared to the formula without the carboethoxyacetyl-3,3-dimethylcyclohexane at the rate of 0.01% (100 ppm) in water and evaluated by a bench panel.

The flavor containing the 1(carboethoxyacetyl)-3,3-dimethylcyclohexane is found to have substantially sweeter aroma notes and a sweet raspberry, raspberry kernel-like and sweet aftertaste and mouthfeel missing in the basic raspberry formulation. It is the unanimous opinion of the bench panel that the chemical 1(carboethoxyacetyl)-3,3-dimethylcyclohexane rounds the flavor out and contributes to a very natural fresh aroma and taste as found in full ripe raspberries. Accordingly, the flavor with the addition of the 1(carboethoxyacetyl)-3,3-dimethylcyclohexane is considered as substantially better than the flavor without 1(carboethoxyacetyl)-3,3-dimethylcyclohexane.

EXAMPLE V

A. Powder Flavor Composition

20 Grams of the flavor composition of Example IV is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F., and a wheel speed of 50,000 r.p.m.

B. Sustained Release Flavor

The following mixture is prepared:

| Ingredient | Parts by Wgt. |
|---|---|
| Liquid Raspberry Flavor Composition of Example IV | 20.00 |
| Propylene glycol | 9.00 |
| Cab-O-Sil ® M-5 (Brand of Silica produced by the Cabot Corporation of 125 High Street, Boston, Mass. 02110; Physical Properties: Surface Area: 200 m²/gm Nominal particle size: 0.012 microns Density: 2.3 lbs/cu.ft. | 5.00 |

The Cab-O-Sil is dispersed in the liquid raspberry flavor composition of Example IV with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE VI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example IV is added to the solution which is then homogenized to form an emulsion having particle size typically in the range of 2–5 microns. This material is kept at 120° F. under which conditions the gelatin will not gel.

Coascervation is induced by adding, slowly and uniformly 40 parts by weight of a 20% aqueous solution of sodium sulphate. During coascervation, the gelatin molecules are deposited uniformly about each oil droplet as a nucleus.

Gelation is effected by pouring the heated coascervation mixture into 1,000 parts by weight of 7% aqueous solution of sodium sulphate at 65° F. The resulting gelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE VII

100 Parts by weight of chicle are mixed with 4 parts by weight of the flavor prepared in accordance with Example V(B). 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE VIII

Chewing Gum

100 Parts by weight of chicle are mixed with 18 parts by weight of the flavor prepared in accordance with Example VI 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE IX

Toothpaste Formulation

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N—Lauroyl Sarcosinate (foaming agent) |
| Group "D" | |
| 1.200 | Flavor Material of Example V(B) |
| 100.00 (Total) | |

Procedure

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strength intensity throughout said procedure (1-1.5 minutes)

EXAMPLE X

Chewable Vitamin Tablets

The flavor material produced according to the process of Example V(B) is added to a Chewable Vitamin Tablet Formulation at a rate of 10 gm/Kg which Chewable Vitamin Tablet Formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.0 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example V(B) | (as indicated above) |
| Sweeteners—sodium saccharin | 1.0 |
| Magnesium stearate lubricant | 20.0 |
| Mannitol q.s. to make | 500.0 |

Preliminary tablets are prepared by slugging with flat-faced punches and grinding the slugs to 14 mesh. 13.5 Grams dry Vitamin A Acetate and 0.6 grams Vitamin D are then added as beadlets. The entire blend is then compressed using concave punches at 0.5 grams each.

Chewing of the resultant tablets yields a pleasant, long lasting, consistently strong raspberry flavor for a period of 12 minutes.

What is claimed is:

1. A process for augmenting or enhancing the raspberry aroma or taste of a consumable material selected from the group consisting of foodstuffs and chewing gums comprising the step of adding to a foodstuff or chewing gum from 0.5 parts per million up to about 100 parts per million based on the total weight of consumable material of at least one compound defined according to the structure:

wherein R represents $C_1$-$C_3$ lower alkyl.

2. The process of claim 1 wherein R represents ethyl.

* * * * *